(12) United States Patent
Layman, Jr. et al.

(10) Patent No.: US 8,648,140 B2
(45) Date of Patent: Feb. 11, 2014

(54) TOLUENE AND STYRENE DERIVED TELOMER DISTRIBUTIONS AND BROMINATED FLAME RETARDANTS PRODUCED THEREFROM

(75) Inventors: William J. Layman, Jr., Baton Rouge, LA (US); Charles H. Kolich, Baton Rouge, LA (US); Arthur G. Mack, Prairieville, LA (US); Steven A. Anderson, Baton Rouge, LA (US); Jonathan P. McCarney, Baton Rouge, LA (US); Junzuo Wang, Little Rock, AR (US)

(73) Assignee: Albemarle Corporation, Richmond, VA (US)

( * ) Notice: Subject to any disclaimer, the term of this patent is extended or adjusted under 35 U.S.C. 154(b) by 297 days.

(21) Appl. No.: 13/130,098

(22) PCT Filed: Nov. 30, 2009

(86) PCT No.: PCT/US2009/066121
§ 371 (c)(1),
(2), (4) Date: Sep. 13, 2011

(87) PCT Pub. No.: WO2010/065462
PCT Pub. Date: Jun. 10, 2010

(65) Prior Publication Data
US 2011/0224363 A1 Sep. 15, 2011

Related U.S. Application Data

(60) Provisional application No. 61/119,271, filed on Dec. 2, 2008.

(51) Int. Cl.
*C08L 55/02* (2006.01)

(52) U.S. Cl.
USPC ........... 524/464; 524/565; 524/577; 524/589; 524/594; 252/609

(58) Field of Classification Search
USPC ....................................................... 524/464
See application file for complete search history.

(56) References Cited

U.S. PATENT DOCUMENTS

| | | | |
|---|---|---|---|
| 2,243,543 A | 5/1941 | ter Horst |
| 2,757,146 A | 7/1956 | Fawcett |
| 2,914,489 A | 11/1959 | Hall |
| 2,954,412 A | 9/1960 | Wulf et al. |
| 3,221,068 A | 11/1965 | Gorham |
| 3,372,880 A | 3/1968 | O'Hara |
| 3,373,135 A | 3/1968 | Jenkner et al. |
| 3,451,988 A | 6/1969 | Langer, Jr. |
| 3,458,586 A | 7/1969 | Langer, Jr. |
| 3,536,679 A | 10/1970 | Langer, Jr. |
| 3,541,149 A | 11/1970 | Langer, Jr. |
| 3,594,396 A | 7/1971 | Langer, Jr. |
| 3,634,548 A | 1/1972 | Harwell et al. |
| 3,668,263 A | 6/1972 | Morrison et al. |
| 3,725,368 A | 4/1973 | Morrison et al. |
| 3,742,077 A | 6/1973 | Kamienski et al. |
| 3,751,384 A | 8/1973 | Langer, Jr. |
| 3,751,501 A | 8/1973 | Kamienski et al. |
| 3,850,882 A | 11/1974 | Underwood et al. |
| 3,943,195 A | 3/1976 | Naarmann et al. |
| 4,041,088 A | 8/1977 | Bach et al. |
| 4,074,032 A | 2/1978 | Naarmann et al. |
| 4,078,019 A | 3/1978 | Langer, Jr. |
| 4,107,231 A | 8/1978 | Wurmb et al. |
| 4,108,921 A | 8/1978 | Langer, Jr. |
| 4,129,551 A | 12/1978 | Rueter et al. |
| 4,129,705 A | 12/1978 | de Zarauz |
| 4,134,938 A | 1/1979 | Langer, Jr. |
| 4,137,212 A | 1/1979 | Theysohn et al. |
| 4,143,221 A | 3/1979 | Naarmann et al. |
| 4,151,223 A | 4/1979 | Neuberg et al. |
| 4,200,702 A | 4/1980 | Gausepohl et al. |
| 4,268,705 A | 5/1981 | Palmer |
| 4,311,818 A | 1/1982 | Sigwalt et al. |
| 4,360,455 A | 11/1982 | Lindenschmidt et al. |
| 4,435,312 A | 3/1984 | Lecolier et al. |
| 4,450,259 A | 5/1984 | Roggero et al. |
| 4,463,135 A | 7/1984 | Maly |
| 4,482,677 A | 11/1984 | Teranaka et al. |
| 4,535,135 A | 8/1985 | Lecolier et al. |
| 4,636,540 A | 1/1987 | Warfel |
| 4,701,498 A | 10/1987 | Roggero et al. |
| 4,734,461 A | 3/1988 | Roggero et al. |
| 4,753,745 A | 6/1988 | Kostusyk et al. |
| 4,755,573 A | 7/1988 | Aycock |
| 4,829,135 A | 5/1989 | Gunesin et al. |
| 4,853,440 A | 8/1989 | Roggero et al. |
| 4,883,846 A | 11/1989 | Moore et al. |
| 4,950,721 A | 8/1990 | Dias et al. |
| 4,975,496 A | 12/1990 | Tigner et al. |
| 5,112,897 A | 5/1992 | Dever et al. |
| 5,112,898 A | 5/1992 | Dever et al. |

(Continued)

FOREIGN PATENT DOCUMENTS

CN 100369941 C 2/2008
DE 1570376 7/1969

(Continued)

OTHER PUBLICATIONS

DIC Corporation, Epoxy Resins, Brominated Flame Retardant Pratherm, from website http://www.dic.co.jp/en/products/epoxy/pratherm.html, 1 page.

(Continued)

*Primary Examiner* — Doris Lee
(74) *Attorney, Agent, or Firm* — James A. Jubinsky

(57) ABSTRACT

This invention relates to novel and useful toluene and styrene derived telomer distributions, such distributions being desirable substrates for the preparation of brominated flame retardants.

22 Claims, No Drawings

(56) References Cited

U.S. PATENT DOCUMENTS

| | | | |
|---|---|---|---|
| 5,196,622 A | 3/1993 | Pettijohn et al. |
| 5,198,594 A | 3/1993 | Lillwitz et al. |
| 5,302,768 A | 4/1994 | Hussain |
| 5,310,858 A | 5/1994 | Greiner et al. |
| 5,326,836 A | 7/1994 | Hwang et al. |
| 5,457,248 A | 10/1995 | Mack et al. |
| 5,625,017 A | 4/1997 | Morita et al. |
| 5,637,650 A | 6/1997 | Gill et al. |
| 5,654,384 A | 8/1997 | Halasa et al. |
| 5,677,390 A | 10/1997 | Dadgar et al. |
| 5,686,538 A | 11/1997 | Balhoff et al. |
| 5,687,090 A | 11/1997 | Chen et al. |
| 5,728,782 A | 3/1998 | Brady et al. |
| 5,741,949 A | 4/1998 | Mack |
| 5,767,203 A | 6/1998 | Ao et al. |
| 5,852,131 A | 12/1998 | Balhoff et al. |
| 5,852,132 A | 12/1998 | Dadgar et al. |
| 5,902,865 A | 5/1999 | Gausepohl et al. |
| 5,916,978 A | 6/1999 | Ao et al. |
| 6,008,283 A | 12/1999 | Rose et al. |
| 6,025,450 A | 2/2000 | Lawson et al. |
| 6,093,211 A | 7/2000 | Hamielec et al. |
| 6,133,381 A | 10/2000 | Reed et al. |
| 6,207,765 B1 | 3/2001 | Ao et al. |
| 6,232,393 B1 | 5/2001 | Dadgar et al. |
| 6,232,408 B1 | 5/2001 | Dadgar et al. |
| 6,235,831 B1 | 5/2001 | Reed et al. |
| 6,235,844 B1 | 5/2001 | Dadgar et al. |
| 6,313,230 B1 | 11/2001 | Tsai et al. |
| 6,326,439 B1 | 12/2001 | Dadgar et al. |
| 6,348,166 B1 | 2/2002 | Knoll et al. |
| 6,355,194 B1 | 3/2002 | Agur et al. |
| 6,362,293 B1 | 3/2002 | Newman et al. |
| 6,521,714 B2 | 2/2003 | Kolich et al. |
| 6,657,028 B1 | 12/2003 | Aplin et al. |
| 6,759,498 B2 | 7/2004 | Ikematsu et al. |
| 6,767,960 B2 | 7/2004 | Bae et al. |
| 6,933,343 B2 | 8/2005 | Ikematsu et al. |
| 7,288,612 B2 | 10/2007 | Desbois et al. |
| 7,351,777 B2 | 4/2008 | Moore et al. |
| 7,425,290 B2 | 9/2008 | Semen |
| 7,632,893 B2 | 12/2009 | Kolich et al. |
| 2002/0035214 A1 | 3/2002 | Gill et al. |
| 2002/0183465 A1 | 12/2002 | Babcock et al. |
| 2005/0143526 A1 | 6/2005 | Faust et al. |
| 2005/0209408 A1 | 9/2005 | Lee et al. |
| 2006/0079644 A1 | 4/2006 | Meyer et al. |
| 2007/0004870 A1 | 1/2007 | Kolich et al. |
| 2007/0142566 A1 | 6/2007 | Kolich et al. |
| 2007/0185280 A1 | 8/2007 | Luther |
| 2007/0232759 A1 | 10/2007 | Chun et al. |
| 2010/0184941 A1 | 7/2010 | Layman, Jr. et al. |

FOREIGN PATENT DOCUMENTS

| | | |
|---|---|---|
| DE | 1589700 | 7/1970 |
| DE | 2050009 | 5/1971 |
| DE | 2758781 | 7/1979 |
| DE | 19516563 A1 | 11/1996 |
| EP | 0000141 A1 | 1/1979 |
| EP | 0002514 B2 | 6/1979 |
| EP | 0277429 B1 | 8/1988 |
| EP | 0334715 B1 | 9/1989 |
| EP | 0741147 A1 | 11/1996 |
| EP | 0775719 A2 | 5/1997 |
| EP | 0806437 A1 | 11/1997 |
| GB | 1107898 | 3/1968 |
| GB | 1174845 | 12/1969 |
| GB | 1270318 | 4/1972 |
| GB | 1342101 | 12/1973 |
| GB | 1536762 | 12/1978 |
| GB | 1589700 | 5/1981 |
| GB | 2164051 A1 | 3/1986 |
| JP | 59-155454 | 9/1984 |
| JP | 62-042938 A | 2/1987 |
| JP | 08-188622 | 7/1996 |
| JP | 09-249705 A1 | 9/1997 |
| JP | 09-249706 A1 | 9/1997 |
| JP | 10-182730 A1 | 7/1998 |
| JP | 11-043511 A1 | 2/1999 |
| JP | 11-080220 A1 | 3/1999 |
| JP | 11-116613 A1 | 4/1999 |
| JP | 2001-341246 A1 | 12/2001 |
| WO | 90/15095 A1 | 12/1990 |
| WO | 99/25746 A1 | 5/1999 |
| WO | 99/55770 A1 | 11/1999 |
| WO | 00/15678 A1 | 3/2000 |
| WO | 02/72645 A1 | 9/2002 |
| WO | 03/020826 A1 | 3/2003 |
| WO | 2005/118245 A1 | 12/2005 |
| WO | 2007/005233 A1 | 1/2007 |
| WO | 2007/076369 A1 | 7/2007 |
| WO | 2008/011477 A1 | 1/2008 |
| WO | 2008/066970 A1 | 6/2008 |
| WO | 2008/154453 A1 | 12/2008 |
| WO | 2008/154454 A1 | 12/2008 |
| WO | 2009/148464 A1 | 12/2009 |
| WO | 2010/065462 A1 | 6/2010 |
| WO | 2010/065464 A1 | 6/2010 |
| WO | 2010/065467 A1 | 6/2010 |
| WO | 2010/065468 A1 | 6/2010 |
| WO | 2010/127072 A1 | 11/2010 |
| WO | 2010/127087 A1 | 11/2010 |
| WO | 2010/127091 A1 | 11/2010 |

OTHER PUBLICATIONS

Eberhardt, G. G., et al., "A Catalytic Telomerization Reaction of Ethylene with Aromatic Hydrocarbons", J. Org. Chem., vol. 29, 1964, pp. 2928-2932.

Eberhardt, G. G., et al., "Telomerization Reactions Involving a N-Chelated Organo Lithium Catalyst", Polymer Preprints, 1972, vol. 13, pp. 667-671.

Feil, F., et al., "Benzyl Complexes of the Heavier Alkaline-Earth Metals: The First Crystal Structure of a Dibenzylstrontium Complex", Organometallics, 2001, vol. 20, pp. 4616-4622.

CAPLUS Abstract of Fujimoto, T., et al., "Preparation of monodisperse polystyrenes with high molecular weights", Polymer Journal, 1975, 7(3), pp. 397-401. 1 page.

Gatzke, A.L., "Chain Transfer in Anionic Polymerization. Determination of Chain-Transfer Constants by Using Carbon-14-Labeled Chain Transfer Agents", Journal of Polymer Science, Part A-1, 1969, vol. 7, pp. 2281-2292.

Science Direct Abstract of Helary, G., et al., "Etude de la polymerisation anionique du styrene en milieu non polaire, en presence de N,N,N',N' tetramethyl ethylene diamine", European Polymer Journal, 1978, vol. 14, issue 5, pp. 345-348. 1 page.

Hennion, G. F., et al., "The Polybromination of Alkylbenzenes", J. Am. Chem. Soc., 1946, vol. 68, issue 3, pp. 424-426.

ICL Industrial Products, F-3014-End Capped Brominated Epoxy, from website http://www.icl-ip.com/Brome/Brome.nsf/viewGetMain/Product350-40/$file/F-3014.pdf, 1 page.

CAPLUS Abstract of Ito, M., et al., "Synthesis of well-defined block copolymers containing poly(N-isopropylacrylamide) segment by anionic block copolymerization of N-methoxymethyl-N-isopropylacrylamide", Designed Monomers and Polymers, 2004, 7(1-2), pp. 11-24. 1 page.

Junkui, C., "Synthesis of Narrow Distribution Polystyrene in RLi-Ligand Complex Systems", Chemical Journal of Chinese Universities, 1989, vol. 10, No. 12, pp. 1246-1250. Abstract only translated.

CAPLUS Abstract of Kalnins, K., et al., "Electronic structure of complexes of benzyl anion and ion pairs with styrene", Vysokimolekulyarnye Soedineniya, Seriya A (1990), 32(2), 316-21. 1 page.

Lamneck, Jr., J. H., "Bromination of the Two Propylbenzenes and Three Butylbenzenes", J. Am. Chem. Soc., 1954, vol. 76, issue 4, pp. 1106-1107.

CAPLUS Abstract of Langer, A. W., Jr., "Reactions of Chelated Organolithium Compounds", Transactions of the New York Academy of Sciences, 1965, 27(7), pp. 741-747. 1 page.

(56) References Cited

OTHER PUBLICATIONS

Marechal, Jean-Marc, et al., "Stereoregulation in the anionic polymerization of styrene initiated by superbases", Polymer, 2003, vol. 44, pp. 7601-7607.
Marechal, Jean-Marc, et al., "Stereospecific anionic polymerization of styrene initiated by R2Mg/ROMt 'ate' complexes", Polymer, 2004, 45, pp. 4641-4646.
Maruoka, K., et al., "Novel Anionic Oligomerization by a New, Sequential Generation of Organolithium Compounds", Macromolecules, 1996, 29, pp. 3328-3329.
Milner, R., et al., "Anionic telomerization of butadiene with toluene and diphenylmethane: microstructure and molecular weight", Polymer, vol. 26, 1985, pp. 1265-1267.
Mizuno, T., et al., "Second and Third Virial Coefficients of Polystyrene with Benzyl Ends near the Theta Point", Macromolecules, 2005, 38, pp. 4432-4437.
Advanced Organic Chemistry, Reactions, Mechanisms, and Structure, 4th Ed., Jerry March, J. Wiley & Sons, 1992, pp. 743-744.
Atkins, Physical Chemistry, P. W., 4th Ed., W. H. Freeman and Co., 1990, p. 800.
Baskaran, D., et al., "Effect of Chelation of the Lithium Cation on the Anionic Polymerization of Methyl Methacrylate Using Organolithium Initiators", Macromolecules, 1995, 28, pp. 7315-7317.
Bildmann, U. J., et al., "Synthesis and Structure of the Tmeda Adduct of a Dibenzyl Lithiate Anion Containing Four-Coordinate Lithium", Organometallics, 2001, 20, pp. 1689-1691.
CAPLUS Abstract of Chakrapani, S., et al., "Strategies for the controlled, living anionic polymerization of acrylic and methacrylic monomers and novel star polymers", Polymer Science, 1994, vol. 1, pp. 112-117. 1 page.
Concise, Polymeric Materials Encyclopedia, Editor-in-Chief, Joseph C. Salamone, CRC Press, 1999, pp. 1305-1307.
CAPLUS Abstract of Morton, M., "Homogeneous anionic polymerization. II. Molecular weight of polystyrene initiated by lithium alkyls", Journal of Polymer Science, 1963, Part A-1, pp. 461-474. 1 page.
CAPLUS Abstract of Narita, T., et al., "Reactivity of butyllithium-MeOCH2CH2OLi System as catalyst for copolymerization of styrene with 1,3-butadiene", Journal of Macromolecular Science, Chemistry, 1970, 4(2), pp. 277-294. 1 page.
Patterman, S. P., et al., "Pi Complexation in Ion Pair Bonding. The Structure of Benzyllithium Triethylenediamine", J. Am. Chem. Soc., 1970, 92:5, pp. 1150-1157.
Pines, H., et al., "Sodium-catalyzed side chain aralkylation of alkylbenzenes with Styrene", J. Am. Chem. Soc, 1958, vol. 80(22), pp. 6001-6004.
Pines, H., et al., "Sodium Catalyzed Reactions. II. Side-chain Ethylation of Alkyl Aromatic Hydrocarbons Catalyzed by Sodium", J. Am. Chem. Soc., 1955, vol. 77(3), pp. 554-559.
Reed, J. N., "Product Subclass 13: Benzyllithium Compounds and (Lithiomethyl)Hetarenes", Science of Synthesis, 2006 (vol. date 2005), vol. 8A, pp. 329-355.
Seki, A., et al., "Crossed aldol reaction using cross-linked polymer-bound lithium dialkylamide", Tetrahedron, 2004, vol. 60, pp. 5001-5011.
Sorenson, W. R., et al., Preparative Methods of Polymer Chemistry, Interscience Publishers, Inc., 1961, pp. 198-200.
Strohmann, C., et al., "A Highly Diastereomerically Enriched Benzyllithium Compound: The Molecular Structure and the Stereochemical Course of Its Transformations", Organometallics, 2002, vol. 21, pp. 3079-3081.
Tsukahara, Y., et al., "Preparation and Characterization of alpha-benzyl-omega-vinylbenzyl Polystyrene Macromonomer", Polymer Journal, 1994, vol. 26, No. 9, pp. 1013-1018.
CAPLUS Abstract of Waack, R., et al., "Effects of lithium halides on the reactivity of organolithium compounds (in polymerization)", Chemistry & Industry, 1964, vol. 12, pp. 496-497. 1 page.
Waack, R., et al., "Reactivities of Organolithium Compounds in Tetrahydrofuran. I. As Vinyl Polymerization Initiators", J. Org. Chem., 1967, 32(11), pp. 3395-3399.
Wilhelm, D., et al., "Reactions of Polyanions Derived from Alkylbenzenes", J. Am. Chem. Soc., 1984, 106, pp. 361-367.

TOLUENE AND STYRENE DERIVED TELOMER DISTRIBUTIONS AND BROMINATED FLAME RETARDANTS PRODUCED THEREFROM

REFERENCE TO RELATED APPLICATIONS

This application is the National Stage of International Patent Appl. No. PCT/US09/066,121 filed on Nov. 30, 2009, which in turn claims the benefit of U.S. Provisional Patent Appl. No. 61/119,271, filed on Dec. 2, 2008, the disclosures of which are incorporated herein by reference.

TECHNICAL FIELD

This invention relates to novel and useful toluene and styrene derived telomer distributions, such distributions being desirable substrates for the preparation of brominated flame retardants. In addition, this invention relates to the brominated flame retardants produced from such telomer distributions.

BACKGROUND

Various brominated aromatics are known flame retardants for thermoplastics. For example, brominated polystyrenes are accepted as commercially significant flame retardants for use in a variety of thermoplastics. These brominated flame retardants have a high aromatic bromine content and, to the extent possible, a low thermally labile bromine content. However, a high aromatic bromine content can be accompanied by a higher than desired thermally labile bromine content. The thermally labile bromine content of a brominated flame retardant is determined by measurement of the HBr off-gas generated when the flame retardant is heated at an elevated temperature for a period of time. The thermally labile bromine content is dependent on (a) the content of HBr by-product still entrapped in the flame retardant (even after finishing steps to reduce this content) and (b) the amount of molecular, non-aromatic bromine present. Examples of non-aromatic bromine are aliphatic bromides, where the aliphatic group is either an alkylene or alkylidene group serving as a bridging group between aromatic groups or is an alkyl substituent on an aromatic group. No matter the source, HBr off-gas from the flame retardant used in the thermoplastic formulations can result in damage to molding equipment used to fabricate thermoplastic formulations at elevated temperatures into articles, e.g., TV enclosures and the like. Thus, there is a need to have a brominated flame retardant having a low thermally labile bromine content.

Fortunately, the amount of entrapped HBr can be and is significantly reduced by water quenching the crude flame retardant reaction mass, followed, as needed, by further finishing treatment, be it by chemical treatment or by water washing. Usually, the removal of entrapped HBr is effective and thus, its contribution to the thermally labile bromine content of the finished brominated flame retardant product is not significant.

Reduction of the other source of HBr off-gas, i.e., the chemically bonded molecular non-aromatic bromide, is more problematic. There are few satisfactory options available in as much as the techniques used for entrapped HBr reduction are of minimal use against the much more stubborn non-aromatic bromine. In the case of brominated styrenic polymers it has been possible, by ingenuously modifying the bromination process parameters and reactant feeds, to diminish the formation of non-aromatic bromine as is evidenced by HP 7010 and HP 3010 flame retardant products of Albemarle Corporation. These commercial products exhibit a thermally labile bromine content of less than 500 ppm while still providing up to about 68 wt % of aromatic bromine in the product.

It would be a desirable contribution to the art if a way could be found of providing new highly aromatic, relatively low molecular weight hydrocarbon raw materials that can be effectively brominated to form brominated flame retardants that exhibit a very high aromatic bromine content (i.e., >72 wt % of bromine), but which at the same time, have a commercially acceptable low thermally labile bromine content.

This invention is deemed to provide such a contribution to the art.

BRIEF SUMMARY OF THE INVENTION

This invention relates, among other things, to a telomer distribution derived by the anionic, chain transfer addition of styrene monomers to toluene and previously formed toluene-styrene telomers. The telomer distributions are comprised of molecules of the formula

Ph-CH$_2$[—CH$_2$CH(Ph)]$_n$-CH$_2$CH$_2$-Ph wherein each Ph is a phenyl group, for each molecule in the distribution, "n" is a whole number in the range of 0 to 6. The preferred telomer distributions are enriched in molecules having an "n" value within the range of from about 0 to about 2.

Telomer distributions of this invention favor molecular populations in which the "n" value range is low as compared to oligomeric distributions, which oligomeric distributions have an "n" value in the range of from 7 to 25 and as compared to polymeric distributions in which the "n" value range is from 26 to 80. There are benefits realized by using telomer mixtures in which "n" is from 0 to 6. First, obtaining a very high Br wt % is facilitated for the telomer distributions of this invention. For example, the brominated flame retardants of this invention can have very high aromatic bromine contents, exceeding 72 wt % bromine. Such brominated flame retardants can be readily blended with a variety of thermoplastic polymers. Secondly the telomer distributions of this invention present fewer sites for the formation of non-aromatic bromine, a thermally labile species, than is the case for distributions in which "n" is from 7 to 25 or 26 to about 80. Indeed, in the telomer distributions of this invention the amount, if any, of molecules having an "n" value greater than 6 is minimal, usually less than about 2 GPC area %.

Also provided by this invention are brominated telomer distributions characterized by one or more of the following brominated telomer distributions:

(a) a distribution of molecules of the formula

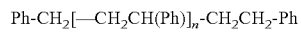
Ph-CH$_2$[—CH$_2$CH(Ph)]$_n$-CH$_2$CH$_2$-Ph wherein each Ph is a brominated phenyl group having between 1 and 5 bromine atoms, and for each molecule in the distribution, "n" is a whole number in the range of 0 to 6, and wherein, (i) at least about 46 GPC area % of the molecules have an "n" value equaling 0, (ii) about 1 to about 26 GPC area % of the molecules have an "n" value equaling 1, and (iii) 0 to about 14 GPC area % of the molecules have an "n" value equaling 2;

(b) a distribution of molecules of the formula

Ph-CH$_2$[—CH$_2$CH(Ph)]$_n$-CH$_2$CH$_2$-Ph;

wherein each Ph is a brominated phenyl group having between 1 and 5 bromine atoms, and for each molecule in the distribution, "n" is a whole number in the range of 0 to 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein, as the value of n increases from 1 to 6, the amount of the corresponding brominated telomer progressively decreases;

(c) a non-polymeric and non-oligomeric distribution of molecules of the formula

Ph-CH$_2$[—CH$_2$CH(Ph)]$_n$-CH$_2$CH$_2$-Ph, wherein each Ph is a phenyl group having between 1 and 5 bromine atoms, and, for each molecule in the distribution, "n" is a whole number in the range of 0 to 6 and wherein the distribution includes molecules having "n" values from 1 to 6.

The above and other aspects, features, embodiments, and advantages of this invention will become still further apparent from the ensuing description and appended claims.

FURTHER DETAILED DESCRIPTION OF THE INVENTION

Telomer Distributions of this Invention

The telomer distributions included in this invention are characterized by one or more of the following:

(a) a distribution of molecules of the formula

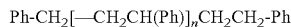

Ph-CH$_2$[—CH$_2$CH(Ph)]$_n$CH$_2$CH$_2$-Ph wherein each Ph is a phenyl group, for each molecule in the distribution, "n" is a whole number in the range of 0 to 6, and wherein, (i) at least about 46 GPC area % of the molecules have an "n" value equaling 0, (ii) about 1 to about 26 GPC area % of the molecules have an "n" value equaling 1, and (iii) 0 to about 14 GPC area % of the molecules have an "n" value equaling 2;

(b) a distribution of molecules of the formula

Ph-CH$_2$[—CH$_2$CH(Ph)]$_n$CH$_2$CH$_2$-Ph;

wherein each Ph is a phenyl group, for each molecule in the distribution, "n" is a whole number in the range of 0 to 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein the GPC area % for "n" equals 1>"n" equals 2>"n" equals 3>"n" equals 4>"n" equals 5>"n" equals 6;

(c) a non-polymeric and non-oligomeric distribution of molecules of the formula

Ph-CH$_2$[—CH$_2$CH(Ph)]$_n$CH$_2$CH$_2$-Ph, wherein each Ph is a phenyl group, and, for each molecule in the distribution, "n" is a whole number in the range of 0 to 6 and wherein the distribution includes molecules having "n" values from 1 to 6.

Preferred telomer mixtures have telomer distributions as presented above with reference to the formula, which distributions are characterized by having a content of from about 46 to about 76 GPC area % for molecules having "n"=0; from about 16 to about 26 GPC area % for molecules having "n"=1; and from about 1 to about 14 GPC area % for molecules having "n"=2.

Further preferred telomer mixtures have telomer distributions as presented above with reference to the formula, which distributions are characterized by having a content of (i) from about 76 to about 95 GPC area % of the molecules having an "n" value equaling 0, (ii) from about 17 to about 5 GPC area % of the molecules having an "n" value equaling 1, and (iii) from about 5 to 0 GPC area % of the molecules having an "n" value equaling 2.

Still further preferred telomer mixtures have telomer distributions as presented above with reference to the formula, which distributions are characterized by having a content of (i) from about 95 to about 99 GPC area % of the molecules having an "n" value equaling 0, and (ii) from about 5 to about 1 GPC area % of the molecules having an "n" value equaling 1.

While, the GPC area % for molecules having an "n" value of 0, 1, and 2, or 0 and 1 are recited above that is not to mean that no other molecules having an "n" value outside of 0 to 2 or 0 to 1 can be present. Rather, the characterization of the feeds by only reciting the GPC area % for molecules of the population, "n"=0 to 2, or 0 to 1 highlights the importance of this limited population and the higher GPC area % numbers associated therewith. See, Examples 1-7 wherein products produced fall within the foregoing characterization, but also have populations of molecules, though not large, having "n" values greater than 2 or 1.

As used above, the term "non-polymeric" is to be taken in the context of the OECD definition of "polymer".

"A chemical substance consisting of molecules characterized by the sequence of one or more types of monomer units and comprising a simple weight majority of molecules containing at least three monomer units which are covalently bound to at least one other monomer unit or other reactant and which consists of less than a simple weight majority of molecules of the same molecular weight. Such molecules must be distributed over a range of molecular weights wherein differences in the molecular weight are primarily attributable to differences in the number of monomer units."

The telomer distributions of this invention can be obtained by the anionic, chain transfer terminated, addition of 1 to about 7 styrene units to toluene using catalytic quantities of lithium reagents complexed with poly(tertiary amines). The telomerization process features the use of toluene as both reactant (chain transfer agent) and as reaction solvent. More, specifically, the process is effected by adding styrene to a reaction mixture initially formed from toluene, catalytic quantities of an alkyllithium (preferably butyllithium) and N,N,N',N'-tetramethylethylenediamine (TMEDA). The reaction mass temperature should be within the range of from about 85° C. to about 115° C. during the addition. This addition reaction is an anionic, chain transfer addition reaction. Further details on the anionic, chain transfer addition reaction that can be used to make the telomeric distribution feeds used in the processes of this invention can be found in commonly owned PCT Application Number PCT/US08/66219, filed Jun. 6, 2008, and which claims the benefit of U.S. Provisional Application No. 60/942,599, filed Jun. 7, 2007, and which PCT Application is incorporated herein by reference as if fully set forth. Examples 1-7 illustrate methods for obtaining telomeric distributions of this invention.

Example 1

A dry 500-mL 4-necked, oil-jacketed glass flask was equipped with a thermocouple, glass overhead stirrer with glass paddle, condenser and N$_2$ inlet. The reactor was charged with 150 mL (130.5 g, 1.55 mol) anhydrous toluene and then subsequently with 2.7 mL (0.0054 mol) n-butyllithium (2M in cyclohexane) and 0.72 mL (0.56 g, 0.0048 mole) TMEDA at ambient temperature. The temperature of the reaction mixture was increased to 110° C. Styrene (50 mL, 45 g, 0.43 mol) was pumped into the reactor at over 137 minutes at a constant rate while maintaining constant and significant agitation of the mixture. Upon completion of the styrene feed, 20 mL anhydrous toluene was pumped into the reaction mixture to clear the feed line of styrene. The reaction mixture was then cooled to 80° C. and then quenched with 0.5 mL isopropyl alcohol. After cooling to room temperature and settling of the lithium isopropoxide salts, the reactor was sampled for GPC analysis. The GPC area % analysis excluding unreacted toluene was as follows: $C_{15}H_{16}$ 64.3%; $C_{23}H_{24}$ 23.4%; $C_{31}H_{32}$ 8.2%; $C_{39}H_{40}$ 2.9%; $C_{47}H_{48}$ 0.9%; $C_{55}H_{56}$ 0.3%; $C_{63}H_{64}$ 0%; $C_{71}H_{72}$ 0%; $C_{79}H_{80}$ 0%; $C_{87}H_{88}$ and higher oligomers 0%.

Example 2

The procedure of Example 1 was used except that 45 g (0.43 mole) of styrene was fed over 127 minute period to a reaction mass formed from 130.5 g (1.55 mole) anhydrous toluene, 1.8 mL (0.0036 mole) 2 M n-butyl lithium and 0.42 g (0.0036 mole) of TMEDA. The GPC area % analysis excluding unreacted toluene was as follows: $C_{15}H_{16}$ 46.1%; $C_{23}H_{24}$ 25.5%; $C_{31}H_{32}$ 13.6%; $C_{39}H_{40}$ 7.2%; $C_{47}H_{48}$ 3.8%; $C_{55}H_{56}$ 1.7%; $C_{63}H_{64}$ and higher oligomers 2%.

Example 3

The procedure of Example 1 was used except that 60.9 g (0.58 mole) of styrene was fed over 173 minute period to a reaction mass formed from 115.0 g (1.25 mole) anhydrous toluene, 2.4 mL (0.00487 mole) 2 M n-butyl lithium and 0.57 g (0.00487 mole) of TMEDA. The GPC area % analysis excluding unreacted toluene was as follows: $C_{15}H_{16}$ 64.8%; $C_{23}H_{24}$ 22.3%; $C_{31}H_{32}$ 7.6%; $C_{39}H_{40}$ 3.0%; $C_{47}H_{48}$ 1.9%.

Example 4

Reactor System

A spherical glass 12-liter creased reactor with oil jacket was equipped with a reflux condenser, distillation head, submerged thermocouple, bottom drain valve, and stainless steel internal cooling coils. Temperature was tightly maintained at a set point via PID controller that regulates water flow to the cooling coils. Vigorous agitation was accomplished by means of an overhead stirring assembly comprised of a 19 mm OD glass shaft with two sets of glass impellers, one set pitched and the other flat, fused to the shaft. The reactor is essentially free of all wetted PTFE parts or other polymeric fluorinated materials or elastomers.
Feeding Techniques The reactor was maintained under an inert dry $N_2$ atmosphere during all operations. The reactor was charged with the chain transfer agent(s) through a dip leg by means of a diaphragm pump. Alkyl lithium, additional solvents and the amine promoter TMEDA were all fed subsurface to the stirred chain transfer agent(s) through the same dip leg. Styrene was pumped into the reactor by means of a metering pump through a 3" cylindrical column (1.75" dia. ≈100 g) of Basic Aluminum Oxide (EMD Chemicals, Aluminum oxide 90, mesh 70-230, column chromatography grade) and delivered as a fine stream or spray above the surface of the reaction mixture through two ¹⁄₁₆" OD feed nozzles.
Detailed Procedure Toluene 2913 g, (3.4 liters, 31.61 mol) was charged to the reactor previously heated to 115° C. The toluene is refluxed and azeotropically dried over a 4 hour period; Karl Fischer moisture analysis indicated 21 ppm of residual $H_2O$, this toluene was dried with 1.5 g of n-BuLi solution. The dried toluene was cooled to 82° C. with the oil jacket and PID controller operating the coiling coils both set at that temperature. Upon cooling to the set point temperature, 63 g n-BuLi solution (2M in cyclohexane, 0.162 mol) was charged through the dip leg below the surface of the gently agitated (300 rpm) toluene reaction mixture. The feed line was then flushed with 75 mL of anhydrous toluene. Next, 46.4 g of TMEDA (0.399 mol) was charged to the reactor through the subsurface feed line forming the characteristic bright red color of TMEDA-complexed benzyl lithium anion with concomitant off-gassing of butane. The subsurface line was flushed with a second 75 mL aliquot of anhydrous toluene via the metering pump. Reactor agitation was increased to 510 rpm and 1713 g of styrene (99+%, 16.45 mol) dissolved in 3070 g of toluene were fed over 360 minutes. The well-calibrated metering pump was programmed to feed at a constant rate of 13.3 g/min. Anhydrous cyclohexane (2×200 mL) was charged to the styrene feed system to flush the alumina bed. The styrene feed to the reactor was deemed complete when no further heat of reaction was observed generally signified by the closing of the automated control valve on the cooling coils. The set point of PID temperature controller was maintained at 82° C. and water was fed through the cooling coils as needed while the flow of the hot oil was altered to bypass the reactor jacket. The reaction mixture was quenched at 75° C. with a 50 mL aliquot of deoxygenated water resulting in a water-white turbid mixture. The reaction mixture was washed with deoxygenated water (3×650 mL). Phase cuts were rapid and required little settling time. Water and any rag or emulsion was removed through the bottom drain valve. During the course of the 6-hour feed, an aliquot was removed after 3 hours for analysis. The GPC area % analysis (excluding unreacted toluene) was as follows: $M_n$=226, $M_w$=247 $M_z$=281, PD=1.091 $C_{15}H_{16}$ 70.3%; $C_{23}H_{24}$ 20.1%; $C_{31}H_{32}$ 6.4%; and higher oligomers 3.2%. The temperature of the oil jacket was increased to 130° C. while the control valve to the cooling coils turned off. Cyclohexane, residual moisture and toluene are distilled through a simple distillation head (1 atm.) until a pot temperature of 114° C. was observed. An aliquot was removed for analysis via GPC, the composition of the reaction product mixture (a telomer distribution of this invention) was as follows: $C_{15}H_{16}$ 75.7%; $C_{23}H_{24}$ 17.4%; $C_{31}H_{32}$ 4.7%; and higher telomers 2.2%.

It will thus be seen that the isolated telomer distribution of this invention formed in this Example 4 was composed of 1,3-diphenylpropane (75.7 GPC area %), 1,3,5-triphenylpentane (17.4 GPC area %), 1,3,5,7-tetraphenylheptane (4.7 GPC area percent), and 2.2 GPC area % of higher telomer(s), which presumably was mainly or entirely 1,3,5,7,9-pentaphenylnonane. Its GPC profile was as follows: $M_n$=219, $M_w$=238 $M_z$=269, PD=1.087.

Example 5

A dry 500-mL 4-necked, oil-jacketed glass flask was equipped with a thermocouple, glass overhead stirrer with glass paddle, condenser and nitrogen inlet. The reactor was charged with 175 mL (151.4 g, 1.64 mol) of anhydrous toluene and then subsequently with 2.24 g (0.0082 mol) of n-butyl lithium (23.5 wt % in cyclohexane) and 2.97 mL (2.29 g, 0.0197 mol) of TMEDA at ambient temperature. The temperature of the reaction mixture was increased to 85° C.

Styrene (94.6 mL, 86 g, 0.83 mol) and toluene (175 mL 151.4 g, 1.64 mol) were mixed and pumped into the reactor at over 359 minutes at a constant rate while maintaining constant and significant agitation of the mixture at a temperature of 85° C. Upon completion of the styrene feed, 20 mL anhydrous toluene was pumped into the reaction mixture to clear the feed line of styrene. The reaction mixture was then cooled to 80° C. and then quenched with 0.5 mL of isopropyl alcohol. After cooling to room temperature and settling of the lithium isopropoxide salts, the reactor was sampled for GPC analysis. The GPC area % analysis (excluding unreacted toluene) of this reaction product mixture was as follows: $M_n$=203, $M_w$=210 $M_z$=220, PD=1.033 with $C_{15}H_{16}$ 86.3%; $C_{23}H_{24}$ 11.9%; $C_{31}H_{32}$ 1.8%; and higher oligomers 0%.

It will thus be seen that the unisolated telomer distribution of this invention formed in this Example 5 was composed of 1,3-diphenylpropane (86.3 GPC area %), 1,3,5-triphenylpentane (11.9 GPC area %), and 1,3,5,7-tetraphenylheptane (1.8 GPC area %).

Example 6

A dry 500-mL 4-necked, oil-jacketed glass flask was equipped with a thermal couple, glass overhead stirrer with glass paddle, condenser and $N_2$ inlet. The reactor was charged with 150 mL (130.5 g, 1.55 mol) of anhydrous toluene and then subsequently with 2.7 mL (0.0054 mol) of n-butyl lithium (2 M in cyclohexane) and 2.42 mL (1.88 g, 0.0162 mole) of TMEDA at ambient temperature. The temperature of the reaction mixture was increased to 110° C. Styrene (50 mL, 45 g, 0.43 mol) dissolved in 150 mL of toluene was pumped into the reactor over a period of 56 minutes at a constant rate while maintaining constant and significant agitation of the mixture with the temperature held at 110-115° C. Upon completion of the styrene feed, 20 mL anhydrous toluene was pumped into the reaction mixture to clear the feed line of styrene. The reaction mixture was then cooled to 80° C. and then quenched with 0.5 mL isopropyl alcohol. After cooling to room temperature and settling of the lithium isopropoxide salts, the reactor was sampled for GPC analysis. The GPC area % analysis excluding unreacted toluene was as follows: $M_n$=214, $M_w$=225 $M_z$=243, PD=1.054 $C_{15}H_{16}$ 84.5%; $C_{23}H_{24}$ 13.1%; $C_{31}H_{32}$ 2.3%; $C_{39}H_{40}$ 0.2% and higher oligomers 0%.

It will thus be seen that the unisolated telomer distribution of this invention formed in this Example 6 was composed of 1,3-diphenylpropane (84.5 GPC area %), 1,3,5-triphenylpentane (13.1 GPC area %), 1,3,5,7-tetraphenylheptane (2.3 GPC area %), and 1,3,5,7,9-pentaphenylnonane (0.2 GPC area %).

Example 7

A glass-lined, 100-gallon jacketed reactor equipped with an overhead condenser, submerged thermal well/thermal couple and a bottom drain valve. Temperature was maintained at a set point by controlling the temperature of the water flowing through the jacket using a steam control valve. Vigorous agitation was accomplished by means of a three-blade, retreat-curve agitator on a variable speed drive. The reactor is essentially free of all wetted PTFE parts or other polymeric fluorinated materials or elastomers.

The reactor was maintained under an inert dry $N_2$ atmosphere during all operations. The reactor was charged with the chain transfer agent(s) through a dip leg by means of pressure transfer from a portable tank. Alkyl lithium, additional solvents and the amine promoter (TMEDA) were all fed subsurface to the stirred chain transfer agent(s) through the same dip leg. Styrene was pressure transferred from a portable, pressure vessel by means of a metering valve through a 24" cylindrical column (3" dia. ≈6 lbs.) of 3 Å mol sieves (Zeochem) and delivered as a fine stream or spray above the surface of the reaction mixture through a slit feed nozzle.

Toluene 140 pounds, (689 mol) was charged to the reactor; Karl Fischer moisture analysis indicated 7 ppm residual $H_2O$. Agitation began. The solvent was heated to 78° C. by applying tempered water to the vessel jacket. Upon reaching the set point temperature, 4.07 pounds of TMEDA (15.9 mol) in 10 pounds of toluene (49.24 mol) was charged to the reactor through the dip leg below the surface of the agitated toluene reaction mixture. The feed line was then flushed with 21 pounds (103 mol) of anhydrous toluene. Next, 3.9 lb n-BuLi solution (23.5 wt % in cyclohexane) (6.53 mol n-BuLi) was charged through the subsurface feed line forming the characteristic bright red-orange color of TMEDA complexed benzyl lithium anion with concomitant off gassing of butane. The feed line was then flushed with 21 pounds (103 mol) of anhydrous toluene. 374.4 lb of styrene (99+%, 1629 mol, American Styrenics) were fed over 162 minutes. The styrene was added by means of pressure transfer from a nitrogen regulated portable tank through a metering valve at a constant feed rate of 2.31 lb/min. The reactor was allowed to ride for 5 minutes to make certain the reaction was complete.

The reaction mixture was quenched at 70° C. with 10 gallons of 0.75 wt % ammonium chloride solution which had been deoxygenated overnight. The reaction mixture was washed with a second 10 gallons of deoxygenated water. Phase cuts were rapid and required little settling time. Water and any rag or emulsion was removed through the bottom drain valve.

The reactor was heated to atmospheric boiling point using tempered water on the vessel jacket. Steam was then applied to the reactor jacket to increase the temperature of the reactor jacket to 140° C. Cyclohexane, residual moisture and toluene boiled, condensed in the overhead condenser, and drained to a drum until a pot temperature of 135° C. was observed. The reactor was cooled to 50° C. Vacuum was applied to the vessel and the reactor was heated to boiling point. Steam was then applied to the reactor jacket to increase the temperature of the reactor jacket to 140° C. Vacuum was used to decrease the reactor pressure to 35 mm Hg. Cyclohexane, residual moisture and toluene boiled, condensed in the overhead condenser, and drained to a drum until a pot temperature of 135° C. was observed. An aliquot was removed from the reactor for analysis via GPC ($M_p$: 301, $M_n$: 433, $M_w$: 626, $M_z$: 883, PD: 1.45). The reaction mass (443 lbs) was collected in a 350-gallon tote bin.

A 3893 g sample of the crude plant-stripped reaction mixture was stripped using a wiped film evaporator (WFE) via continuous operation of residual toluene and 1,3-diphenylpropane (to 1.0 GPC area % max specification) to yield 3111 g of a product that had the following GPC analysis: $M_p$: 409, $M_n$: 543, $M_w$: 698, $M_z$: 907, PD: 1.29. WFE operating conditions were as follows: feed rate=1.33 L/hr, oil jacket temperature=155° C., Pressure=<0.1 mmHg and condenser temperature=0° C. Additionally the cold finger condensed 784 g of a mixture having the following GPC analysis: $M_n$=204, $M_w$=212, PD=1.04 with $C_{15}H_{16}$ 80.65%; $C_{23}H_{24}$ 17.7%; $C_{31}H_{32}$ 1.5%; and $C_{39}H_{40}$ 0.2%.

It will thus be seen that this condensate, a telomer distribution of this invention, was composed of 1,3-diphenylpropane (80.65 GPC area %), 1,3,5-triphenylpentane (17.7 GPC area %), 1,3,5,7-tetraphenylheptane (1.5 GPC area %), and 1,3,5,7,9-pentaphenylnonane (0.2 GPC area %).

The GPC area % values set forth in Examples 1 through 7 were obtained by GPC (described in more detail below) using an oligopore column which provided baseline to baseline resolution of the individual telomers as well as partially resolved any accompanying short chain oligomers. It is therefore possible to discuss these product mixtures in terms of the relative formation of discrete molecules. The resulting data demonstrates that a variety of mixtures of telomers can be prepared under different process conditions. The product distributions demonstrate a dependence on the ratio of monomer to chain transfer agent, on the ratio of monomer to the tertiary polyamine complex organolithium initiator, and on the feed rate of the monomer.

Table 1 summarizes the conditions and results for Examples 1-7.

TABLE 1

| | | | Example | | | | | |
|---|---|---|---|---|---|---|---|---|
| | | 1 | 2 | 3 | 4 | 5 | 6 | 7 |
| Styrene/Toluene (vol/vol) | | 0.33 | 0.33 | 0.5 | 0.26 | 0.27 | 0.16 | n/a |
| TMEDA/Butyllithium (mol/mol) | | 1 | 1 | 1 | 2.46 | 2.4 | 3.0 | n/a |
| Styrene/butyllithium (mol/mol) | | 80 | 120 | 120 | 101 | 101 | 80 | n/a |
| Time of Styrene Feed (min) | | 137 | 127 | 173 | 360 | 360 | 56 | n/a |
| Temperature (° C.) | | 110-115 | 110-115 | 110-115 | 82 | 85 | 110-115 | |

| Product | | | GPC | GPC | GPC | GPC | GPC | GPC | GPC |
|---|---|---|---|---|---|---|---|---|---|
| n = | MW | Formula | area % | area % | area % | area % | area % | area % | area % |
| 0 | 196.29 | $C_{15}H_{16}$ | 64.3 | 46.1 | 64.8 | 75.7 | 86.3 | 84.5 | 80.7 |
| 1 | 300.44 | $C_{23}H_{24}$ | 23.4 | 25.5 | 22.3 | 17.4 | 11.9 | 13.1 | 17.7 |
| 2 | 404.59 | $C_{31}H_{32}$ | 8.2 | 13.6 | 7.6 | 4.7 | 1.8 | 2.3 | 1.5 |
| 3 | 508.74 | $C_{39}H_{40}$ | 2.9 | 7.2 | 3 | 2.2 | | 0.2 | 0.2 |
| 4 | 612.89 | $C_{47}H_{48}$ | 0.9 | 3.8 | 1.9 | | | | |
| 5 | 717.04 | $C_{55}H_{56}$ | 0.3 | 1.7 | | | | | |
| 6+ | 821.19 | $C_{63}H_{64}$ | | 2 | | | | | |

Brominated Telomer Distributions of this Invention

The brominated telomer distributions of this invention are characterized by having useful physical properties rendering them suitable for use as flame retardants in various flammable polymeric or resinous substrates. For example, the brominated telomers of this invention case have extremely high bromine contents, e.g., in the range of about 77 wt % to about 81 wt % of bromine. When a material providing a greater melt flow index (MFI) is desired, brominated distributions of this invention having a bromine content in the range of about 72 wt % to about 77 wt % of bromine are highly suitable for this purpose. For use in certain resins for foam applications, such as polyurethanes and expanded polystyrene, where a more highly soluble brominated flame retardant is desired, use can be made of brominated telomers of this invention having a bromine content in the range of about 45 wt % to about 72 wt % of bromine.

Another feature of the brominated telomers of this invention is their thermal stabilities. For example, brominated telomer distributions of this invention can have a thermal HBr content of less than 1000 ppm at 300° C. and less than 300 ppm at 280° C. when measured under a stream of nitrogen. In addition, brominated telomer distributions of this invention can have a TGA weight loss of 5 wt %, which does not occur until a temperature of at least 320° C. is reached.

Still another feature of the brominated telomers of this invention is desirable color characteristics. Brominated telomer distributions of this invention have been prepared having a Hunter Colorimeter Yellowness Index (YI) in accordance with the ASTM D 1925 procedure of less than 10, which is adequate for many applications.

To offset the plasticizing effect of relatively low molecular weight brominated species, it is desirable in some flame retardant applications to provide a flame retardant having a glass transition temperature ($T_g$) in a suitably high range. Experiments have shown that it is possible, pursuant to this invention, to produce brominated telomers in which the $T_g$ is in the range of about 135° C. to about 215° C. Similarly, in such applications, it is desirable to provide a flame retardant having a melting point, as measured by differential scanning calorimetry (DSC), where the melting point minimum occurs at a temperature in the range of about 160° C. to about 310° C. This broad distribution of minimum melting point temperatures, and the foregoing broad range of glass transition temperatures, enable the flame retardant users to have at their disposal, flame retardants tailored to suit the needs of the particular flame retarded polymer composition under consideration.

Particularly preferred brominated styrenic telomer distributions of this invention are those characterized by having greater than about 77 wt % to about 81 wt % bromine content, a thermal HBr value at 300° C. of less than 1000 ppm, a 5 wt % TGA weight loss occurring at not less than 320° C., a Hunter color YI of less than 10, and having $T_g$ in the range of 170° C. to 215° C. and/or having a melting point minimum (DSC) occurring in the range of about 225° C. to about 310° C.

In order to produce a brominated telomer distribution of this invention, any known method for bromination of aromatic hydrocarbons may be employed. In general, the brominations are conducted in the absence of light and preferably use elemental bromine as the brominating agent. The bromination is carried out under anhydrous conditions, using a suitable Lewis acid catalyst such as an aluminum halide or ferric halide catalyst. To minimize bromination on aliphatic carbon atoms, the reaction is preferably conducted at temperatures below about 25° C. A bromination solvent such as, for example, dibromomethane, ethylene dibromide, bromochloromethane, dichloromethane, ethylene dichloride is typically used in the process.

A general description of a preferred bromination procedure used in the practice of this invention is as follows:

Preparation for Bromination

Dichloromethane (DCM) or other suitable bromination solvent was dried (5-40 ppm moisture by Karl Fisher) with activated alumina of Acidic Aluminum Oxide (EMD Chemicals, Aluminum oxide, mesh 70-230, column chromatography grade). All feed lines, feed tanks and glassware were dried (oven dried at 130° C. min 2 hour where appropriate) and purged over-night prior to use in the bromination reaction. All glassware, feed lines, and feed tanks are maintained under a $N_2$ atmosphere during the course of the set-up and the operation of the bromination reactor.

The amount of $AlBr_3$ catalyst (commercially available) needed to make a 0.25 mole % (calculated using the formula [moles $AlBr_3$/moles $Br_2$]*100%=0.25 mole % $AlBr_3$) solution of active catalyst was weighed and then transferred to oven dried reagent bottles in a nitrogen-purged glove box. By active catalyst, it is meant that amount of catalyst above any additional amount that would be otherwise deactivated by moisture either in the bromine itself or any other process stream involved in the bromination reaction. Bromine (5-10 ppm moisture content) was pumped into the reagent bottle containing the $AlBr_3$ and then stirred with a PTFE coated magnetic stirring bar for 30 minutes to assure homogeneous dissolution of the catalyst. The 0.25 mole % $AlBr_3$ in bromine solution was then transferred to a graduated feeding vessel placed on a large capacity laboratory balance.

The anionic chain-transfer styrene Telomer (ACTST) used was dissolved in dry (5-10 ppm moisture) DCM to make a 25-wt % solution. The solution was then charged to a graduated feeding vessel. The 0.25 mole % $AlBr_3$ in bromine and the 25 wt % ACTST in DCM solution are co-fed via separate peristaltic pumps through ⅛" (3.2 mm) O.D. feed lines to a well-stirred fresh or recycle heel of anhydrous DCM at 0° C. to -10° C. The relative feed rates are constantly monitored such that the ratio of the two reagents fed remains constant or near constant during the course of the electrophilic bromination reaction.

Bromination Equipment Set-Up:

A 5 L oil jacketed flask (bromination reactor) was equipped with an overhead glass stirrer shaft, PTFE stiffing paddle, a water-cooled condenser, thermowell, nitrogen inlet, and bottom drain valve. The reactor was vented through a calcium sulfate moisture trap to a well-stirred caustic scrubber to absorb co-product HBr and entrained $Br_2$. Additionally the reactor was outfitted with three inlet lines: 1) ¼" (6.4 mm) O.D. PTFE BCM feed for initial feed of BCM to the reactor (the BCM can be either fresh or a BCM recycle heel from a previous run); 2) ⅛" (3.2 mm) O.D. substrate/BCM subsurface feed line; and 3) ⅛" (3.2 mm) O.D. $Br_2$/$AlBr_3$ subsurface feed line. The $AlBr_3$/$Br_2$ and ACTST/BCM feed lines are secured such that both inlet lines discharge their contents in close proximity creating a locally high reagent concentration. The bromination reactor was completely covered with aluminum foil to exclude light and the reaction was conducted in a darkened ventilation hood.

The bromination reactor was placed above a 6-liter water quench pot with a ⅜" (9.5 mm) O.D. PTFE drain line that connects the bottom drain valve of the bromination reactor to the quench pot to allow for direct transfer of the bromination reactor's contents. The quench pot was oil jacketed and equipped with an over-head stiffing mechanism, thermowell and was baffled for intimate mixing of organic and aqueous phases. The quench pot had a nitrogen inlet and was purged to a caustic scrubber. The quench pot had a bottom drain valve to enable transfer of the pot's contents to an intermediate 5 liter storage vessel.

The intermediate storage vessel was piped to transfer its contents to a wash kettle. The wash kettle was a 6-liter oil-jacketed, baffled reactor outfitted with an over-head stirrer, thermocouple and bottom drain valve.

Product isolation set-up provides a water-containing vessel into which the product slurry is fed accompanied by the concomitant azeotropic removal of DCM. The precipitate from this solvent removal process is collected by filtration or centrifugation and then passed through an oven for drying.

Example 8

Bromination

To the 5 L bromination reactor described above was charged 3320.23 g (4.4 liters) of dry DCM (33 ppm moisture, Karl Fisher). The DCM was cooled in the dark to -1° C. and a previously prepared 25 wt % solution comprised of 200 g of the condensate of Example 7 (which was composed of $C_{15}H_{16}$ 80.65%; $C_{23}H_{24}$ 17.7%; $C_{31}H_{32}$ 1.5%; and $C_{39}H_{40}$ 0.2%) and 399.3 g of dry DCM was charged to a dry, 2000 mL $N_2$ blanketed graduated cylinder outfitted with a ⅛" (3.2 mm) PTFE feed line placed to transfer the entire content of the cylinder by means of a peristaltic metering pump to the bromination reactor. The previously prepared $AlBr_3$ (0.25 mol %) in bromine (1600 g) was transferred via a peristaltic pump into a 1.5 liter graduated cylinder. This feed vessel was maintained under a $N_2$ atmosphere and was outfitted with a ⅛" (3.2 mm) PTFE feed line placed to transfer the desired amount of bromine solution by means of a peristaltic metering pump to the bromination reactor.

The two reagents are co-fed at predetermine relative rates such that the entire content of the two feeds are charged and simultaneously completed in 120 minutes. Ample cooling was provided through out the operation such that the reaction temperature remains close to -2° C. Upon completion of the feed the reaction was allowed to stir for an additional 60 minutes and gradually warmed to 15° C. to allow unreacted bromine to be consumed. The reaction mixture was transferred (gravity) to the 6 L quench pot through the bottom drain valve and the ⅜" (9.5 mm) O.D. PTFE transfer line.

The quench pot was previously charged with 1000 mL tap water (25° C.) and stirred at 400 rpm to assure intimate mixing of the organic and aqueous phase. The quench was exothermic and a 10° C. temperature rise was observed. Agitation was slowed to 20 revolutions per minute and the organic slurry phase allowed to settle. The red bromine/HBr aqueous phase gradually separated forming the top layer. The lower organic slurry phase was transferred to a 5 L storage vessel containing 1000 mL of 10% NaOH.

This two-phase system was then transferred to the 6 L wash kettle and refluxed (39° C.) for 30 minutes. Agitation was interrupted and the bottom organic layer cut from the reactor. The organic layer was returned to the completely drained kettle and washed twice with 1000 mL of tap water until a pH of 10 was observed and the color of the water wash was faint yellow. The organic slurry was then washed with 0.5 wt % sodium borohydride in 2 wt % NaOH at 36° C. The organic slurry was separated and washed a final time with 1000 mL of tap water.

The slurry was placed in a stirred tank and gravity fed to the precipitation reactor (10 liters tap water containing 2 grams $NaBH_4$, 60° C.) with concomitant azeotropic distillation of DCM. Upon completion of the feed the pot temperature was increased to 98° C. and held at that temperature for 20 minutes. The resulting off white product was collected by vacuum filtration rinsed with tap water until the rinse registered a pH<9. The product dried in a nitrogen purged oven at 185° C. to a constant weight, 850 g. The product thus obtained had the analyses shown in Table 2.

TABLE 2

| Bromination Example | | BR-7 |
|---|---|---|
| Wt % Br XRF | | 78.09 |
| Thermal HBr 280° C. (ppm) | | 202 |
| Thermal HBr 300° C. (ppm) | | 540 |
| DSC | $T_g$ (° C.) | 180 |
| | MP (min) (° C.) | 225.67 |
| TGA (° C.) | 1% wt Loss | 259.87 |
| | 5% wt Loss | 322.48 |
| | 10% wt Loss | 342.07 |
| | 50% wt Loss | 390.83 |
| ASTM D 1925 | L | 88.33 |
| | a | 0.12 |
| | b | 4.86 |
| | YI | 9.92 |

Use of the Flame Retardants of this Invention

As noted above, the brominated telomer distributions of this invention (often referred to hereinafter as "flame retardants of this invention") can be used as flame retardants, especially in macromolecular substances such as thermoplastic polymers and thermoset polymers, as well as natural and synthetic elastomers, including thermoplastic polyurethane elastomers, etc.

Illustrative polymers are: olefin polymers, cross-linked and otherwise, for example homopolymers of ethylene, propylene, and butylene; copolymers of two or more of such alkene monomers and copolymers of one or more of such alkene monomers and other copolymerizable monomers, for example, ethylene/propylene copolymers, ethylene/ethyl acrylate copolymers and ethylene/propylene copolymers, ethylene/acrylate copolymers and ethylene/vinyl acetate copolymers; polymers of olefinically unsaturated monomers, for example, polystyrene, e.g. high impact polystyrene, and styrene copolymers, polyurethanes; polyamides; polyimides; polycarbonates; polyethers; acrylic resins; polyesters, especially poly(ethyleneterephthalate) and poly(butyleneterephthalate); polyvinyl chloride; thermosets, for example, epoxy resins; elastomers, for example, butadiene/styrene copolymers and butadiene/acrylonitrile copolymers; terpolymers of acrylonitrile, butadiene and styrene; natural rubber; butyl rubber and polysiloxanes. The polymer may be, where appropriate, cross-linked by chemical means or by irradiation. The flame retardants of this invention can also be used in textile applications, such as in latex-based back coatings.

The amount of a flame retardant of this invention used in a formulation will be that quantity needed to obtain the flame retardancy sought. In general, the formulation and resultant product may contain from about 1 to about 50 wt % of bromine, introduced therein in the form of at least one flame retardant of this invention. Preferably, this amount is in the range of from about 5 to about 30 wt % of bromine, introduced into the substrate polymer in the form of at least one flame retardant of this invention. Masterbatches of polymer are formed from one or more flame retardants of this invention blended with additional amounts of substrate polymer. The amount of flame retardant of this invention used in a masterbatch ordinarily is in the range of 50 to 99 wt %.

It is advantageous to use the flame retardants of this invention in combination with one or more suitable flame retardant synergists, such as antimony-based synergists, e.g. $Sb_2O_3$.

Generally, the flame retardants of this invention will be used with the antimony based synergists in a weight ratio ranging from about 1:1 to 7:1, and preferably of from about 2:1 to about 4:1.

Any of a number of conventional additives used in thermoplastic formulations may be used, in their respective conventional amounts, with the flame retardants of this invention. Examples of such conventional additives include plasticizers, antioxidants, fillers, pigments, UV stabilizers, lubricants, impact modifiers, and the like.

Various procedures for blending the flame retardants of this invention with substrate polymers can be used. Non-limiting examples of such procedures include melt blending, powder blending, and the like.

Thermoplastic articles formed from formulations containing a thermoplastic polymer and a flame retardant of this invention can be produced conventionally, e.g., by injection molding, extrusion molding, compression molding, and the like. Blow molding may also be appropriate in certain cases.

In one of the more particular embodiments of this invention, the flame retardants of this invention can be used in various styrenic polymers, including homopolymers and/or copolymers of various styrenic monomers which typically contain in the range of 6 to 10 aromatic carbon atoms. Examples of such monomers are styrene, alpha-methylstyrene, ortho-methylstyrene, meta-methylstyrene, para-methylstyrene, para-ethylstyrene, isopropenyltoluene, vinylnaphthalene, isopropenylnaphthalene, vinylbiphenyl, the dimethylstyrenes, tert-butylstyrene, and analogous monomers. The flame retardants of this invention with a bromine content in the range of about 72 to about 81 wt %, are especially well suited for use in flame retarding impact modified polystyrenes (e.g., HIPS), styrene-acrylonitrile copolymers (SAN), and impact modified styrene-acrylonitrile copolymers (e.g., ABS).

In another of the more particular embodiments of this invention, the flame retardants of this invention that are comprised of brominated styrene telomers having bromine contents in the range of about 45 to about 72 are suited for use in forming polyurethane foams, such as flexible polyurethane foams. Typically, such telomers and adducts of this invention are introduced into the polyurethane formulation prior to initiation of polymerization. Typically, the telomers and adducts of this invention are predissolved in a liquid phosphate flame retardant such as isopropylated triphenyl phosphates. As is well known in the art, formulations used for preparing flexible polyurethane foams comprise as components or ingredients at least isocyanate, polyol, surfactant, catalyst, and blowing agent. The brominated telomers and adducts of this invention are deemed suitable for use as flame retardant components to be included with such formulations used for preparing polyurethanes. The catalyst is usually added to the formulation as the final ingredient so that polymerization occurs. When the brominated telomers or brominated adducts of this invention are introduced into the polyurethane formulation along with an alkylated triphenyl phosphate such as isopropylated triphenyl phosphate the resultant flexible polyurethane foam is characterized by having good scorch resistance. Alkylated triphenyl phosphates, as well as other known materials are known to also function as flame retardant synergists.

Among particular flame retarded compositions which can be formed by use of a flame retardant of this invention are the following:

A) A HIPS-based formulation containing a flame retardant amount of a brominated flame retardant of this invention. Such formulations can be composed of primarily HIPS or they can be an alloy of HIPS, such as a polyphenylene ether-HIPS blend. These are flame retarded compositions formed by blending a brominated flame retardant of this invention with the HIPS or alloy thereof.

B) An ABS-based formulation containing a flame retardant amount of a brominated flame retardant of this invention. Such formulations can be composed of primarily ABS or they can be an alloy of ABS, such as a polycarbonate-ABS blend. These are flame retarded compositions formed by blending a brominated flame retardant of this invention with the ABS or alloy thereof.

C) A polyolefin-based formulation containing a flame retardant amount of a brominated flame retardant of this invention. Such polyolefin-based formulations include polyethylene, polypropylene, and ethylene or propylene copolymers with other olefinic monomers copolymerizable therewith. These are flame retarded compositions formed by blending a brominated flame retardant of this invention with a polyolefin homopolymer or copolymer.

D) An engineering thermoplastic-based formulation containing a flame retardant amount of a brominated flame retardant of this invention. These are flame retarded compositions formed by blending a brominated flame retardant of this invention with an engineering thermoplastic polymer or blend thereof.

E) A formulation as in D) wherein the engineering thermoplastic is a thermoplastic polyester. These are flame retarded compositions formed by blending a brominated flame retardant of this invention with a thermoplastic polyester or blend thereof.

F) A formulation as in D) wherein the engineering thermoplastic is a thermoplastic polyamide. These are flame retarded compositions formed by blending a brominated flame retardant of this invention with a polyamide thermoplastic or blend thereof.

G) A formulation as in any of A)-F) wherein the flame retardant amount is in the range of about 1 to about 95 wt % based on the total weight of the formulation.

H) A formulation as in any of A)-F) wherein the formulation additionally contains a synergistic amount of a flame retardant synergist.

I) A flame retarded thermoset resin composition which comprises a thermoset resin in which has been included a flame retardant amount of a brominated flame retardant of this invention.

J) A composition as in I) wherein said thermoset resin is a novolak resin.

Analytical Procedures

Known analytical methods can be used or adapted for use in assaying the characteristics of the compositions and formulations of this invention.

GPC wt % Telomer Distributions

The GPC area % values were obtained by GPC using a modular system with a Shimadzu autosampler (model SIL-9), a Shimadzu refractive index detector (model RID-6A), a Waters HPLC pump (model 510) and a Waters TCM column heater. The columns used were Polymer Labs (Varian) Oligopore columns, 300 mm by 7.5 mm, part number 1113-6520. The solvent used was tetrahydrofuran, HPLC grade. The test procedure used entailed dissolving approximately 0.10 g of sample in 10 mL of THF. An aliquot of this solution is filtered and 50 µL is injected on the columns. Based on isolated 1,3-diphenylpropane and 1,3,5-triphenylpentane adducts, and the mode of separation is size exclusion, peaks are identified according to their order of elution as 1,3-diphenylpropane, 1,3,5-triphenylpentane, 1,3,5,7-tetraphenylheptane, 1,3,5,7,9-pentaphenylnonane, etc. The individual peaks of the oligomeric material are then assigned theoretical molecular weight values. A calibration curve is constructed using these theoretical values and their corresponding retention times. Based on this calibration, the overall distribution data is calculated and reported. The calculations were performed by the Viscotek Omnisec, version 4.2.0.237 gel permeation chromatography (GPC) data collection and processing system.

Total Bromine Content (Combustion)

Bromine content of the brominated products produced from the telomers of this invention is typically determined by use of a combustion method. The procedure of this method is as follows:

A 0.04-0.08 g of sample of the Brominated Telomer is weighed on a 0.00001 g accuracy, onto ¼ sheet of creased black filter paper on a 5 place analytical balance. The sample is folded inside the filter paper placed in a platinum sample holder. A combustion flask is prepared by adding 15 mL of caustic aresenite solution and 3 drops concentrated $NH_4OH$. The flask is thoroughly flushed for at least two minutes with oxygen. The platinum sample holder is placed in the top of the combustion flask which is then flushed for at least one more minute. The flask is stoppered and secured so that the flask is gas tight when inverted. Silicone grease is used to form a continuous seal around the entire joint surface. The inverted combustion flask containing the sample is placed into a Thomas-Ogg oxygen flask infrared igniter. The sample is ignited and the residue is dissolved in deionized water made basic with solid KOH and further digested by boiling. The solution is concentrated, cooled and acidified with sulfuric acid. Bromide is then titrated with a 0.1 to 0.01 N $AgNO_3$ standardized solution using a silver titrode on a autotitrator. Wt % Bromine of the brominated telomer is given by the equation below:

$$\text{wt \% } Br = \frac{(S-B)(N)(7.9904)}{\text{Sample Weight in Grams}}$$

where:
S=milliliters of $AgNO_3$ required to titrate the sample
B=milliliters of $AgNO_3$ required to titrate the blank
N=normality of $AgNO_3$ Yellowness Index Hunter Colorimeter In order to assess the color properties of the brominated products formed from the telomers of this invention, the analytical procedure described in ASTM D 1925 was employed.

Thermogravimetric Analysis

Thermogravimetric analysis (TGA) is also used to test the thermal behavior of the flame retardant compositions formed from the telomers of this invention. The TGA values are obtained by use of a TA Instruments Thermogravimetric Analyzer. Each sample is heated on a Pt pan from 25° C. to about 600° C. at 10 C.°/min with a nitrogen flow of 50-60 mL/min.

Thermal Stability Test (Thermally Labile Bromine Test

This test procedure for determining the thermal stability of the brominated flame retardants produced by bromination of the telomers of this invention is a procedure essentially as described in U.S. Pat. No. 5,637,650. In conducting this test, each sample is run in duplicate. A 2.00 g+/−0.01 g sample is placed into a new clean 20 mm by 150 mm test tube. With a neoprene stopper and Viton® fluoroelastomer tubing, the test tube is connected to a nitrogen purge line with exit gas from the test tube being passed successively through subsurface gas dispersion frits in three 250-mL sidearm filter flasks each containing 200 mL of 0.1 N NaOH and 5 drops of phenolphthalein. With a constant nitrogen purge at 0.5 SCFH, the test tube is heated at 300° C. in a molten salt bath (51.3% KNO$_3$/48.7% NaNO$_3$) for 15 minutes followed by 5 minutes at ambient temperature. The test tube containing the sample is then replaced with a clean dry test tube, and the apparatus is purged with nitrogen for an additional 10 minutes with the empty test tube in the 300° C. salt bath. The test tube, tubing and gas dispersion tubes are all rinsed with deionized water, and the rinse is combined quantitatively with the solutions in the three collection flasks. The combined solution is acidified with 1:1 HNO$_3$ and titrated with 0.01 N AgNO$_3$ using an automatic potentiometric titrator (Metrohm 670, 716, 736, or equivalent). Results are calculated as ppm in accordance with the equation:

HBr=(mL AgNO$_3$ to end point)·(normality of AgNO$_3$)
·(80912)/(sample wt.)

The tubing is thoroughly dried with nitrogen before the next analysis. Each day before the first sample, three empty clean test tubes are run as blanks to assure there is no residual hydrogen halide in the system.

T$_g$ Values

T$_g$ values were obtained by DSC with a TA Instruments DSC Model 2920. Samples were heated to 400° C. at a rate of 10 C.°/min under nitrogen. T$_g$ is determined by noting the change in the specific heat of a polymer at the glass to rubber transition. This is a second order endothermic transition (requires heat to go through the transition). In DSC, the transition appears as a step transition and not a peak such as might be seen with a melting transition. See, *The Elements of Polymer Science and Engineering, An introductory Text for Engineers and Chemist*, Alfred Rudin, Academic Press, Orlando Fla., 1982, pg 403.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Each and every patent or publication referred to in any portion of this specification is incorporated in toto into this disclosure by reference, as if fully set forth herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text taken in context clearly indicates otherwise.

The invention may comprise, consist or consist essentially of the materials and/or procedures recited herein.

This invention is susceptible to considerable variation in its practice. Therefore the foregoing description is not intended to limit, and should not be construed as limiting, the invention to the particular exemplifications presented hereinabove.

The invention claimed is:

1. A telomer distribution comprised of one or more of:
   (a) a distribution of molecules of the formula

wherein each Ph is a phenyl group, for each molecule in the distribution, "n" is a whole number in the range of 0 to 6, and wherein,
   (i) at least about 46 GPC area % of the molecules have an "n" value equaling 0,
   (ii) about 1 to about 26 GPC area % of the molecules have an "n" value equaling 1, and
   (iii) 0 to about 14 GPC area % of the molecules have an "n" value equaling 2;
   (b) a distribution of molecules of the formula

wherein each Ph is a phenyl group, wherein for each molecule in the distribution, "n" is a whole number in the range of 0 to 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein the GPC area % for "n" equals 1>"n" equals 2>"n" equals 3>"n" equals 4>"n" equals 5>"n" equals 6;
   (c) a non-polymeric and non-oligomeric distribution of molecules of the formula

wherein each Ph is a phenyl group, and, for each molecule in the distribution, "n" is a whole number in the range of 0 to 6 and wherein the distribution includes molecules having "n" values from 1 to 6.

2. A telomer distribution as in claim 1 wherein the distribution is characterized by having: a content of from about 46 to about 76 GPC area % for molecules having "n"=0; from about 16 to about 26 GPC area % for molecules having "n"=1; and from about 1 to about 14 GPC area % for molecules having "n"=2.

3. A telomer distribution as in claim 1 wherein the distribution is characterized by having:
   (i) from about 76 to about 95 GPC area % of the molecules having an "n" value equaling 0,
   (ii) from about 17 to about 5 GPC area % of the molecules having an "n" value equaling 1, and
   (iii) from about 5 to 0 GPC area % of the molecules having an "n" value equaling 2.

4. A telomer distribution as in claim 1 wherein the distribution is characterized by having:
   (i) from about 95 to about 99 GPC area % of the molecules having an "n" value equaling 0, and
   (ii) from about 5 to about 1 GPC area % of the molecules having an "n" value equaling 1.

5. A brominated telomer distribution characterized by one or more of the following:
   (a) a distribution of molecules of the formula

wherein each Ph is a brominated phenyl group having between 1 and 5 bromine atoms, wherein for each molecule in the distribution, "n" is a whole number in the range of 0 to 6, and wherein,
(i) at least about 46 GPC area % of the molecules have an "n" value equaling 0,
(ii) about 1 to about 26 GPC area % of the molecules have an "n" value equaling 1, and
(iii) 0 to about 14 GPC area % of the molecules have an "n" value equaling 2;
(b) a distribution of molecules of the formula

Ph-CH$_2$[—CH$_2$CH(Ph)]$_n$CH$_2$CH$_2$-Ph;

wherein each Ph is a brominated phenyl group having between 1 and 5 bromine atoms, for each molecule in the distribution, "n" is a whole number in the range of 0 to 6, and wherein the distribution is characterized by a majority of the molecules in the distribution having an "n" value of 0 and a minority, not exceeding 49 GPC area %, of the molecules in the distribution having an "n" value of 1, 2, 3, 4, 5 or 6 wherein the GPC area % for "n" equals 1>"n" equals 2>"n" equals 3>"n" equals 4>"n" equals 5>"n" equals 6;
(c) a non-polymeric and non-oligomeric distribution of molecules of the formula

Ph-CH$_2$[—CH$_2$CH(Ph)]$_n$-CH$_2$CH$_2$-Ph, wherein each Ph is a brominated phenyl group having between 2 and 5 bromine atoms, wherein for each molecule in the distribution, "n" is a whole number in the range of 0 to 6, and wherein the distribution includes molecules having "n" values from 1 to 6.

6. A brominated telomer distribution as in claim 5 having a bromine content in the range of about 77 wt % to about 81 wt % of bromine.

7. A brominated telomer distribution as in claim 5 having a bromine content in the range of about 72 wt % to about 77 wt % of bromine.

8. A brominated telomer distribution as in claim 5 having a bromine content in the range of about 45 wt % to about 72 wt % of bromine.

9. A brominated telomer distribution as in claim 5 having a thermal HBr content of less than 1000 ppm at 300° C. and less than 300 ppm at 280° C.

10. A brominated telomer distribution as in claim 5 having a TGA weight loss of 5 wt % occurring at a temperature not less than 320° C.

11. A brominated telomer distribution as in claim 5 having a Hunter color YI of less than 10.

12. A brominated telomer distribution as in claim 5 having a T$_g$ in the range of 135° C. to 215° C.

13. A brominated telomer distribution as in claim 5 having a differential scanning calorimetry melting point minimum occurring in the range of about 160° C. to about 310° C.

14. A brominated telomer distribution as in claim 5 having:
a bromine content in the range of about 77 wt % to about 81 wt %,
a thermal HBr content of less than 1000 ppm at 300° C.,
a 5 wt % TGA weight loss occurring at not less than 320° C.,
a Hunter color YI of less than 10, and
a T$_g$ in the range of 170° C. to 215° C. and/or a differential scanning calorimetry melting point minimum occurring in the range of about 225° C. to about 310° C.

15. A flame retarded HIPS-based or ABS-based polymer composition containing a flame retardant amount of the composition as in claim 5.

16. A flame retarded thermoset resin composition which comprises a thermoset resin, wherein said thermoset resin is optionally a novolak resin, in which has been included a flame retardant amount of a composition as in claim 5.

17. A composition as in any of claim 15 or 16 wherein said flame retardant amount is in the range of about 1 to about 95 wt % based on the total weight of the composition.

18. A composition as in claim 15 wherein the composition additionally contains a synergistic amount of a flame retardant synergist.

19. A composition as in claim 18 wherein the flame retardant synergist is an antimony-containing synergist.

20. A composition as in any of claims 18-19 wherein the amount of the synergist is in the range of about 1 to about 12 wt % based on the total weight of the composition.

21. A formulation for the preparation of polyurethane, which formulation is characterized by containing, as a flame retardant, a composition of claim 5.

22. A formulation as in claim 21 further comprising at least one flame retardant synergist, wherein said synergist is optionally an alkylated triphenylphosphate.

* * * * *

UNITED STATES PATENT AND TRADEMARK OFFICE
CERTIFICATE OF CORRECTION

PATENT NO.       : 8,648,140 B2
APPLICATION NO. : 13/130098
DATED            : February 11, 2014
INVENTOR(S)      : Layman, Jr. et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this
Twenty-ninth Day of September, 2015

Michelle K. Lee
*Director of the United States Patent and Trademark Office*